United States Patent [19]

Sheehan

[11] Patent Number: 4,970,001
[45] Date of Patent: Nov. 13, 1990

[54] USE OF CHITOSAN TO IMPROVE MEMBRANE FILTER PERFORMANCE

[75] Inventor: John J. Sheehan, Ellicott City, Md.

[73] Assignee: W. R. Grace & Co.-Conn., New York, N.Y.

[21] Appl. No.: 348,339

[22] Filed: May 5, 1989

[51] Int. Cl.$^5$ .............................................. B01D 63/02
[52] U.S. Cl. .................................. 210/638; 210/639; 210/651; 210/500.23; 210/500.27
[58] Field of Search ............... 210/638, 639, 651, 653, 210/500.23, 500.27

[56] References Cited

U.S. PATENT DOCUMENTS 3,228,877  1/1966  Mahon ........................... 210/653 X
4,089,778  5/1978  Gauger ............................... 210/638

OTHER PUBLICATIONS

Rohm & Haas Product Literature, (1987/1988), Knorr, Dietrich; "Functional Properties of Chitin and Chitosan", *J. Food Sci.*, 47, 593–594 (1982).
Bough, Wayne, "Reduction of Suspended Solids in Vegetable Canning Waste Effluents by Coagulation with Chitosan", *J. Food Sci.*, 40, 297–301 (1975).
Bough, Wayne; "Chitosan—a Polymer from Seafood Waste, for Use in Treatment of Food Processing Wastes and Activated Sludge", *Processing Biochemistry*, Jan.-Feb. 1976, pp. 13–16.
Seng, Jean–Marc, "Chitine, Chitosane et Derives: De Nouvelles Perspectives pour L'Industrie"; *Biofutur*, Sep. 1988, 40–44.
Freeman, Karen; "Chitin Companies Not Crabby about Their Prospects for Growth and Profit", *Genetic Eng. News*, Jun. 1987, p. 2.
Amano et al; Filter Papers Containing Chitosan with Cellulose Fibers, Diatomaceous Earth, and/or Pearlite, Mar. 2, 1988, CA 109(22):197232a.
Asao et al.; Manufacture of Chitosan Paper with Good Quality and Increased Tensile Strength, Mar. 15, 1988, CA 109(2):8297s.
Mochizuki et al.; Separation of Liquid Mixtures by Pervaporation Membrane; Jan. 23, 1988, CA 108(20):170105d.
Hashimoto et al.; Low Molecular Weight Chitosans for the Removal of Nucleic Acids and/or Endotoxins from Liquid Samples on Small or Large Scale; CA 108(19):166107p.
Uemura et al.; Porous Polymer Sheets with Moisture Absorbing and Desorbing Properties; Nov. 4, 1987; CA 108(8):57558r.
Furukawa et al.; Chitosan Membranes for Separation of Liquid Mixtures; CA 106(26):215980n.
Morita, I.; Water Purifying Agent, Dec. 20, 1986, CA 106(16):125690p.
Kurita Water Industries, Ltd.; Sludege Dewatering; May 28, 1984; CA 101(18):15714v.
Pittalis et al., Hollow Chitosan Fibers; Apr. 20, 1983; CA 99(6):39744q.
Agency of Industrial Sciences & Technology; Chitosan Membranes Suitable for Ultrafiltration and Dialysis; Jun. 20, 1980; CA 93(24):222510a.
Fujita, T.; Recovery of Proteins; Jan. 17, 1972, CA 76(17):98205n.

*Primary Examiner*—Frank Spear
*Attorney, Agent, or Firm*—Vanessa L. Appleby; Jill H. Krafte; Steven T. Trinker

[57] ABSTRACT

Improvement in cross-flow membrane filtration. Chitosan is admixed with an aqueous dispersion of colloids or finely divided solids to flocculate the solids. The chitosan-flocculated liquid is then filtered on a membrane by cross-flow under pressure. A layer of chitosan-containing flocculant material deposits on the membrane and provides superior flux performance as compared to certain commerical flocculants.

11 Claims, 1 Drawing Sheet

USE OF CHITOSAN TO IMPROVE MEMBRANE FILTER PERFORMANCE

FIELD OF THE INVENTION

The invention relates to the treatment of aqueous dispersions of colloidal or similar finely divided solids, and more specifically relates to cross-flow membrane filtration.

BACKGROUND OF THE INVENTION

A great many aqueous dispersions of colloidal and finely divided materials are made as a result of manufacturing processes. These liquids are commonly concentrated in order to recover liquid or solids or both. By way of example, many fermentation operations require concentration of the cell broth as a preliminary step to recovery of solids for in-plant use, sale, or disposal. Such concentration is conventionally accomplished by adding a flocculant to the cell broth, followed by cross-flow membrane filtration. However crossflow membrane filtration of cells in downstream processing of fermentation broths often suffers from poor flux performance because of fouling by cells depositing on the membrane. The use of synthetic polymeric flocculants (water soluble polymers and solid particle materials) has been suggested as a means of increasing cell particle size, leading to improved fluxes. Larger particle sizes are more readily swept off the membrane surface in crossflow operation. Larger particles which do settle on the membrane form a layer which is more permeable. Thus, synthetic polymers have been shown to improve flux performance. However, due to toxic properties of several of thse polymers, they may be considered unsafe for use in the production of food and pharmaceutical products. Furthermore, there is a need for more effective and/or less costly polymers than those commercially available. Chitosan has been used as a flocculant for cells, but has never been applied specifically for crossflow membrane filtration of fermentation broths, or the like, so far as can be determined from the literature.

SUMMARY OF THE INVENTION

This invention involves the use of chitosan, a natural polymer derived from crustaceans to improve flux performance. The invention provides a means of flocculating cells with a safe, natural polymer which is also more effective than alternative synthetic polymers.

Chitosan is not soluble directly in water. It must first be added to an acid solution to form a soluble ionic derivative. This derivatized chitosan is admixed with an aqueous dispersion of colloids or finely divided solids to flocculate the solids. The treated liquid is then concentrated by contacting it in cross flow under pressure against a semipermeable membrane. The flocculated solids form a unique layer on the membrane that facilitates flux because the particles on the surface form a more permeable layer than untreated particles would. The invention thus involves such layer on a semipermeable membrane as a novel article, together with methods for making and using the article. In preferred embodiments the starting aqueous dispersion is a fermentation broth, and the flocculated solids are thus flocculated cells.

LITERATURE

Bough, Wayne; "Reduction of Suspended Solids in Vegetable Canning Waste Effluents by Coagulation with Chitosan," *J. Food Sci.* 40, 297–301 (1975).

Bough, Wayne; "Chitosan—a Polymer from Seafood Waste, for Use in Treatment of Food Processing Wastes and Activated Sludge," *Process Biochemistry*, Jan/Feb. 1976, pp. 13–16.

Seng, Jean-Marc, "Chitine, Chitosane et Derives: De Nouvelles Perspectives pour L'Industrie"; *Biofutur*, September 1988, 40–44.

OBJECTS OF THE INVENTION

It is an object of the invention to provide improved flux performance in membrane filtration of flocculated colloids or finely divided materials.

Another object is to provide a unique, highly efficient membrane filter aid.

A further object is to accelerate concentration of aqueous colloids and finely divided solids.

A still further object is to form a special flocculated layer of combined chitosan and finely divided material or colloidal material on the surface of a filtration membrane, to aid crossflow filtration through the membrane.

Other objects will be apparent from the description herein.

IN THE DRAWING

THE APPARATUS

Figure 1:
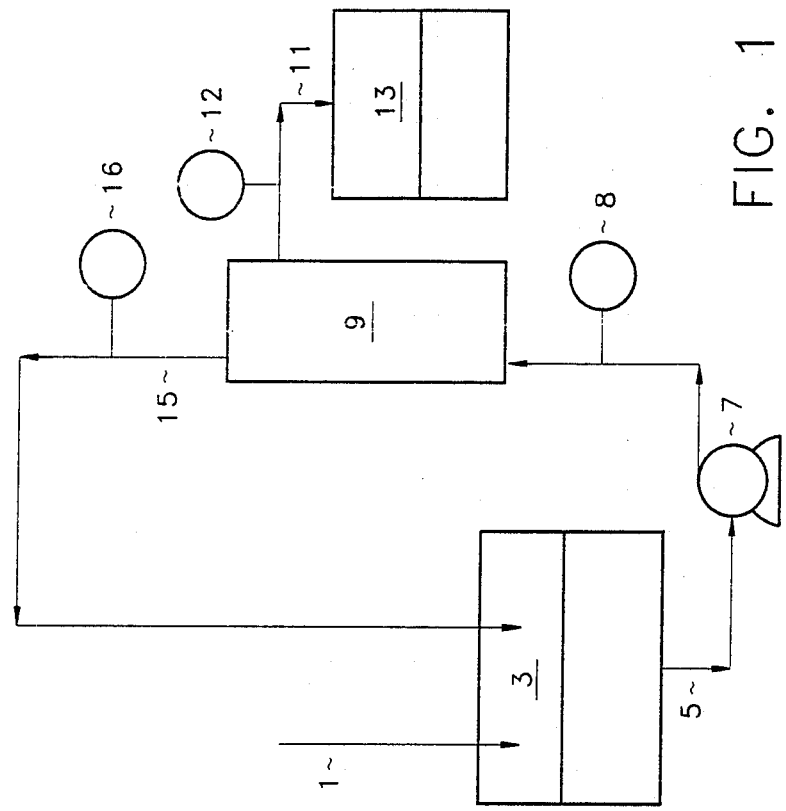
FIG. 1 shows a schematic flow diagram of a process using the invention.

Except for the use of chitosan, the apparatus and process used in concentrating aqueous dispersions of colloids or finely divided solids is conventional. Reference is made to FIG. 1. Line 1 feeds chitosan solution to retentate vessel 3. Retentate is pumped via line 5 and pump 7 to membrane hollow fiber cartridge 9, from which line 11 exits to permeate collection vessel 13. Retentate from cartridge 9 leaves via line 15 and is recycled to retentate vessel 3. Pressure in gauge 8 is suitably about 2–25 psig; in gauge 12 about 0–20 psig;, and in gauge 16 about 0–15 psig. These pressures are not critical.

Although a batch system is shown, obviously the arrangement can be modified to provide for continuous operation, e.g., by continuous addition of chitosan solution and feed liquid to retentate vessel 3, continuous withdrawal of concentrate from Vessel 3, and continuous withdrawal of permeate from cartridge 9. Also, two or more such concentration systems may be used, e.g., in series, parallel, mixed series/parallel, etc., with or without recycle of retentate and/or permeate to various points in the resulting streams.

Conventional arrangements for back-flushing may be used.

As used in the examples, the membrane was a commercially available 0.2 micron polysulfone hollow fiber. Fiber inner diameter was about 1.0 mm. The fibers were pre-assembled as purchased in a cartridge to provide about 0.35 $ft^2$ of membrane surface. (About 40 fibers.) Average pore size was selected as about 0.2 microns, small enough to prevent passage of cells, but large enough, in association with the chitosan-flocculated cell layer, to give good permeation. Pore size should of course be selected with respect to the size of solids being concentrated. Membrane wall thickness is not critical. Typically wall thickness is about 6–10 mils.. The hollow fibers used in my examples were about 10 inches long (functional length).

Other useful membranes include ceramic membranes (e.g. alumina); cellulose and cellulose derivatives, etc.

Membrane configurations useful in my invention are not limited to hollow fibers. Other applicable forms include flat sheet (plates and frames) and tubular systems. Also, my technique applies to a range of membrane materials and pore sizes and includes both ultrafiltration and microfiltration.

Figure 2:
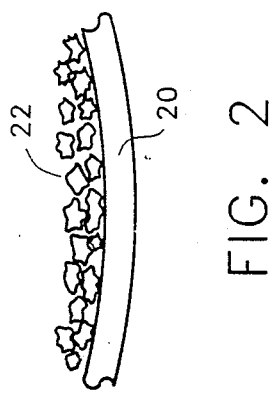
FIG. 2 shows a greatly enlarged partial section of a layer of flocculated colloid or finely divided material on a membrane, as used in the invention process.

In normal operation the chitosan-treated fluid flows through the lumen of the hollow fiber under pressure. During passage, liquid passes through the membrane wall, and then it joins liquid from the other fibers, and is discharged to permeate collection. The removal of liquid thus concentrates the solids left behind in the hollow fiber. The crux of the invention lies in the fact that the use of chitosan as the flocculant deposits clumps or clusters of chitosan-associated solids as a layer on the membrane. Also, it reduces the degree of deposition since larger particles are swept from the surface. This layer is a unique filter aid, speeding passage of liquid through the membrane while at the same time inhibiting clogging of the membrane and in general improving flux as compared to commercially available alternate flocculants. This layer is shown in FIG. 2, which represents a hollow fiber membrane in partial cross section, greatly enlarged, with a layer of chitosan-flocculated solids (in this case, cells) as laid down during operation of the invention process in concentrating E. coli fermentation broth. The membrane wall is shown at 20, the flocculated cell layer at 22.

DETAILED DESCRIPTION OF THE INVENTION

The following examples illustrate without limiting the invention. For these examples, E. coli fermentation broth containing 20 g/liter of cells (dry weight basis) was used as representative of aqueous dispersions that can be treated in accordance with the invention. The cells were cultured in a 14-liter fermentor in a medium containing glucose, hydrolyzed casein, and trace salts.

EXAMPLE 1

Preparation of Chitosan Solution and Its Use in Flocculation

An aqueous solution of chitosan is prepared. This is conveniently done by dissolving chitosan in 1.0-N acetic acid to make a 1% solution. This provides a pH of about 4.0. Various other acids may also be used, e.g. hydrochloric, nitric, etc.. However, chitosan is not soluble in sulfuric acid and has only limited solubility in phosphoric acid at concentrations below 0.5%. This 1% solution is then added to cell broth following completion of fermentation at dosages between 10 and 200 ppm chitosan, followed by gentle mixing for 5 to 10 minutes to allow flocculation to occur. The flocculated broth is then concentrated using a cross flow membrane filter as elsewhere herein described. 0.5 to 2.0 liter volumes of broth were concentrated five-fold to 100 g/liter.

EXAMPLE 2

Three polymeric flocculants were tested:

1. "D"—a polyquaternary amine (conventional water-soluble polymer).
2. "RH"—a polystyrene particle with quaternary amine functional groups.
3. Chitosan (this invention).

The dosages for each flocculant were optimized by running cell concentration tests with a range of dosages. Results are summarized in the Table. Percent flux enhancement is calculated based on control tests run with no flocculant present.

TABLE

Comparison of Commercial Synthetic Flocculants and Chitosan:

Effect on Flux Performance

| Flocculant | Dose (ppm) | % Flux Enhancement |
|---|---|---|
| "D" | 25 | 14 |
|  | 50 | 28* |
|  | 75 | 5 |
| "RH" | 25 | −7 |
|  | 50 | 72* |
|  | 75 | 43 |
| Chitosan | 50 | 124 |
|  | 100 | 260* |
|  | 200 | 153 |

*Indicates optimum dose.

As shown in the Table, chitosan demonstrated an effect on membrane flux performance more than three-fold greater than the best obtained with the two synthetic polymers. Optimal dosages are usually less than 1000 ppm (e.g., 1–1000 ppm), preferably 10–200 ppm. Optimal dose is dependent on type of solids (e.g., cell types), solids concentration, and other factors present in the suspension which influence flocculation.

E. coli broth is not critical in the concentration process. A wide variety of dispersions of colloids and finely divided solids can be concentrated by use of chitosan as herein described. Such liquids include waste waters from breweries, food, poultry processing, and rendering plants; effluent from paper processing; sludge dewatering; and the like. Obviously, the liquid must contain some amount of colloids or finely dispersed solids in order to form the chitosan-flocculant layer on the membrane.

CHITOSAN

Chitosan, a crustacean product, is available commercially in a variety of purities, grades, and particle sizes. Practically all are suitable in this invention. Where a particularly pure permeate or retentate is desired, the purer grades of chitosan are of course preferred. The chitosan used in the herein examples was cream-colored flakes assaying about 90% polyglucosamine and had a molecular weight (weight average) of about 60,000. Molecular weight is not critical. Particle size is generally of little concern, however, since the material is dissolved before use. Chitosan may be prepared by methods described in the literature, e.g., in the article by Seng, supra, and in the article by Bough, *Proc. Biochem.*, supra.

In the claims:

1. Article, a layer of chitosan-flocculated solids on a cross-flow filtratron membrane.

2. Article according to claim 1, wherein the solids comprise fermentation cells.

3. Article according to claim 1, wherein the membrane is a hollow fiber of polysulfone.

4. Article, a cartridge of a plurality of hollow membrane fibers, the interiors of which are coated with a layer of chitosan-flocculated solids.

5. Process comprising:
   (i) admixing an aqueous solution of chitosan with an aqueous dispersion of colloids or finely divided solids, thereby to flocculate the colloids or solids; and
   (ii) passing the said chitosan-treated dispersion to a cross-flow filtration membrane, thereby to pass a permeate through the membrane, with concomitant concentration of the retentate.

6. Process according to claim 5 wherein the chitosan dosage is about 10-200 ppm.

7. Process according to claim 5 wherein the dispersion is fermentation broth.

8. Process according to claim 5 wherein the membrane is polysulfone.

9. Process of concentrating an aqueous dispersion of colloids or finely divided solids wherein a flocculant is added to the dispersion and the thus flocculated dispersion is then concentrated on a cross-flow filtration membrane to provide a permeate and a retentate; characterized in that the flocculant is chitosan.

10. Process according to claim 9 wherein the aqueous dispersion is fermentation broth, the filtration membrane is polysulfone, and the chitosan is added as a 1% solution.

11. A method for increasing flux in cross-flow filtration of an aqueous dispersion of colloids or finely divided solids comprising:
   (1) admixing an aqueous solution of chitosan with an aqueous dispersion of colloids or finely divided solids, thereby to flocculate the colloids or solids; and
   (2) passing said chitosan-treated dispersion to a cross-flow filtration membrane, thereby to pass a permeate through the membrane, with concomitant concentration of the retentate.

* * * * *